United States Patent [19]
Kaminski et al.

[11] Patent Number: 5,724,142
[45] Date of Patent: Mar. 3, 1998

[54] METHOD AND APPARATUS FOR MEASURING AND CONTROLLING THE VOLUME OF A LIQUID SEGMENT IN A TUBE

[75] Inventors: Edward Stephen Kaminski, North East, Md.; Paul John Zuk, Lincoln University, Pa.

[73] Assignee: Dade International Inc., Deerfield, Ill.

[21] Appl. No.: 619,069

[22] Filed: Mar. 29, 1996

[51] Int. Cl.⁶ .................................................. G01B 11/28
[52] U.S. Cl. ........................................ 356/379; 250/577
[58] Field of Search ............................... 356/379, 380, 356/128, 134, 133; 250/577

[56] References Cited

U.S. PATENT DOCUMENTS

| | | |
|---|---|---|
| 3,636,360 | 1/1972 | Oishi et al. .................... 250/577 |
| 4,210,809 | 7/1980 | Pelavin . | |
| 4,989,452 | 2/1991 | Toon et al. . | |
| 5,074,658 | 12/1991 | Tavlarides et al. .................... 356/379 |

FOREIGN PATENT DOCUMENTS

| | | |
|---|---|---|
| 0 289 833 A2 | 11/1988 | European Pat. Off. . |
| PCT/AU93/ 00232 | 5/1993 | WIPO . |
| WO 93/24811 | 12/1993 | WIPO . |
| WO 94/03780 | 2/1994 | WIPO . |

*Primary Examiner*—F. L. Evans
*Attorney, Agent, or Firm*—Leland K. Jordan; Lois K. Ruszala

[57] ABSTRACT

A method for measuring or controlling the volume of a liquid segment confined within a tube and having a leading edge and a trailing edge. The tube is exposed to radiation at an angle and radiation refracted from the inner surface of the tube is measured at the leading and trailing edges of the segment while the liquid segment is moving through the tube.

13 Claims, 4 Drawing Sheets

METHOD AND APPARATUS FOR MEASURING AND CONTROLLING THE VOLUME OF A LIQUID SEGMENT IN A TUBE

BACKGROUND OF THE INVENTION

1. Field of the Invention

The present invention is related to the field of liquid pumping devices and more particularly to a method and apparatus for precisely measuring or controlling the volume of a fluid being pumped. Although not limited to the field of automated clinical analyzers, the present invention is particularly useful when applied therein.

2. Description of The Prior Art

Automated clinical chemistry analyzers are well known in the art and generally use a pumping device such as a diastolic pump or a piston pump to transfer predetermined volumes of liquid samples or liquid reagents bet-ween receptacles, such as sample liquid containers, reagent liquid containers and reaction cuvettes or vessels disposed at various locations on the analyzer. A common problem with such pumping devices is measuring and controlling the volume of liquids being transferred and various techniques have been used in the past.

Within the clinical chemistry industry, the desire to minimize the quantity of bodily fluids extracted from a patient is in conflict with the desire to perform a larger number of analytical tests to provide accurate and rapid diagnosis. One solution to this problem is to miniaturize reaction vessels so that either smaller patient sample liquids are extracted or that more analytical tests may be performed using an extracted patient sample liquid. For this reason, the need to precisely measure very small quantities liquid samples or liquid reagents is becoming urgent. These quantities are in the range of 0.1 to 1 microliters and the difficulties in delivering such small volumes is exacerbated by the need to control the volume within an accuracy of ±0.5%. For example, sample liquid volume deficiencies may create serious analytical errors in automated assays for calcium, magnesium and glucose, in particular.

U.S. Pat. No. 4,210,809 (Pelavin) provides for precise liquid segment measurements by using signals generated by a pair of sensors precisely spaced apart a predetermined distance to determine the time of passage of the leading edge of a liquid segment between the two sensors in combination with a signal from single one of the sensors to determine the time of passage of the entire liquid segment. This method depends upon radiation transmission through the liquid segment and is limited to measuring the volume of segments that are constituted by liquids that have essentially the same energy transmission characteristics and is also limited to liquids that have relatively minimal energy losses due to refraction and/or absorption of the transmitted radiation. It is desirable to remove this limitation so that the measurement technique and the method of pumping control is not restricted to the handling of certain liquids.

PCT International Application No. WO 93/24811 (Watt et als) describes a method for measuring the mass flow rates of liquid phases in a liquid segment comprising at least two liquid phases, the phases having different radiation absorption characteristics. The method employs two spaced apart dual energy transmission gauges or sensors to determine the time of passage of a liquid segment between the two sensors. The leading edge of a segment is detected by the observation of several consecutively increasing measurements of radiation attenuation and the trailing edge of a segment is detected by the observation of several consecutively decreasing measurements of radiation attenuation. The difference in absorption of radiation which is transmitted through the different liquid phases is used to calculate the mass rate of flow of the different liquid phases within the liquid segment. This technique requires knowledge of the radiation absorption within the two liquid phases during transmission of the radiation through the liquid segment.

It is therefore believed to be advantageous to provide a liquid pumping method which accurately measures very small quantities of liquids using a single sensor and which is not dependent upon the absorption characteristics of the liquids so that an unrestricted variety of liquids may be pumped. It is also believed to be advantageous to provide a liquid pumping method which effectively controls the pumping of very small quantities of liquids using a single sensor, thereby avoiding unnecessary complexity of the control means of the instrument.

SUMMARY OF THE INVENTION

The present invention relates to a method for determining the volume of a liquid segment having a leading edge and a trailing edge and being confined within a tube. The volume is determined using a single radiation detector to measure an amount of radiation refracted at the interface between the inner wall of the tube and the liquid segment by exposing the tube to radiation incident at an azimuthal angle, measured about the axis of the tube that maximizes the amount of radiation reaching the detector when the tube contains no liquid. The refracted radiation is measured firstly, when there is no liquid present in the tube; secondly, at the appearance of the leading edge of the segment; and thirdly, at the appearance of the trailing edge of the segment. Knowing the tube diameter and the time of passage of the liquid segment determines the liquid volume.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
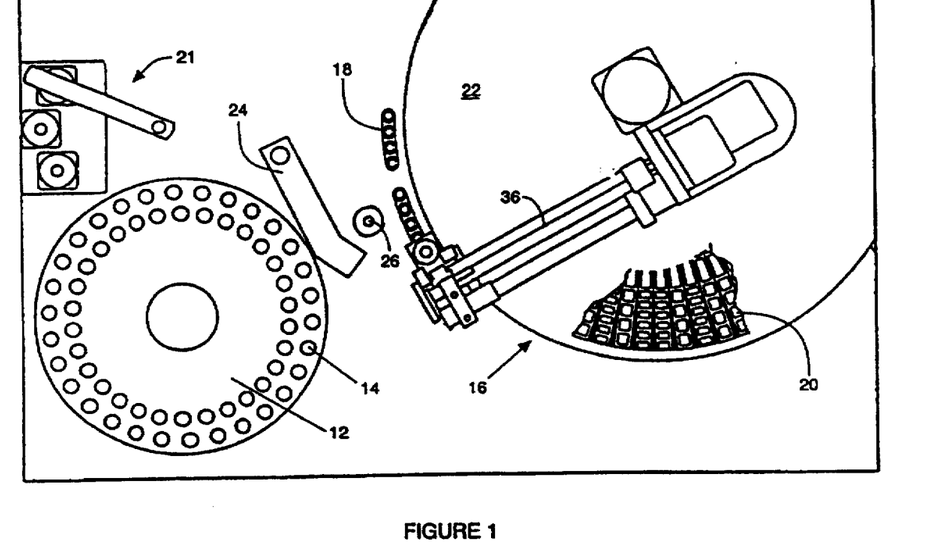
FIG. 1 is a schematic plan diagram of an automated chemical analyzer in which the present invention may be used to advantage.

FIG. 1 shows schematically the elements of a conventional automated chemical analyzer 10 comprising a sample liquid carousel 12 used to support a plurality of sample liquid containers 14 and a reaction cuvette carousel 16 adapted to receive a plurality of reaction cuvettes 18. A plurality of reagent liquid cartridges 20 are disposed within the reaction cuvette carousel 16 beneath a lid 22 (shown with a cut out portion to reveal the reagent liquid cartridges 20) which covers various thermally controlled areas during operation. A secondary analytical module 21 operating independently of the reaction cuvettes 18 may be present in analyzer 10. Reagent cartridges 20 are preferably a multi-compartmented container such as those sold under the tradename FLEX™ by E. I. du Pont de Nemours and Co., Inc., Wilmington, Del. Reaction cuvettes 18 are formed by pulling two different composition ribbons of clear film from a cuvette film cartridge, not shown, onto the periphery of the cuvette carousel 16. The cuvette carousel 16, preferably in the form of a wheel, has about 100 separate cuvette cavities, the inner wall of each cavity having an inner wall to allow transmission of light. A small opening remains at the top of the reaction cuvette 18 to allow the addition of reagent liquid and sample liquid. A rotatable sample liquid arm 24 and wash resource 26 are located proximate the sample liquid carousel 12 and cuvette carousel 16.

Figure 2:
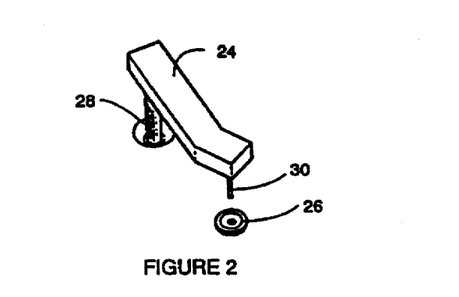
FIG. 2 is a perspective view of a liquid dispensing apparatus of FIG. 1.

FIG. 2 shows sample liquid arm 24 mounted to a rotatable shaft 28 so that, taken with FIG. 1, movement of a sample liquid arm 24 describes an arc intersecting all three components 12, 16, and 26. A hollow, sample liquid probe 30, supported by sample liquid arm 24, is adapted to aspirate and discharge liquids, for example, from a sample liquid container 14 and into a cuvette 18. A reagent liquid arm 36 of conventional design draws reagent liquid from an appropriate reagent liquid cartridge 20 and deposits reagent liquid within a predetermined reaction cuvette 18 and ultrasonically mixes the reagent liquid and chase water. Photometic analyzing means, not shown, located beneath the cuvette carousel 16 measures radiation absorbance through the cuvette 18 at various wavelengths.

Figure 3:
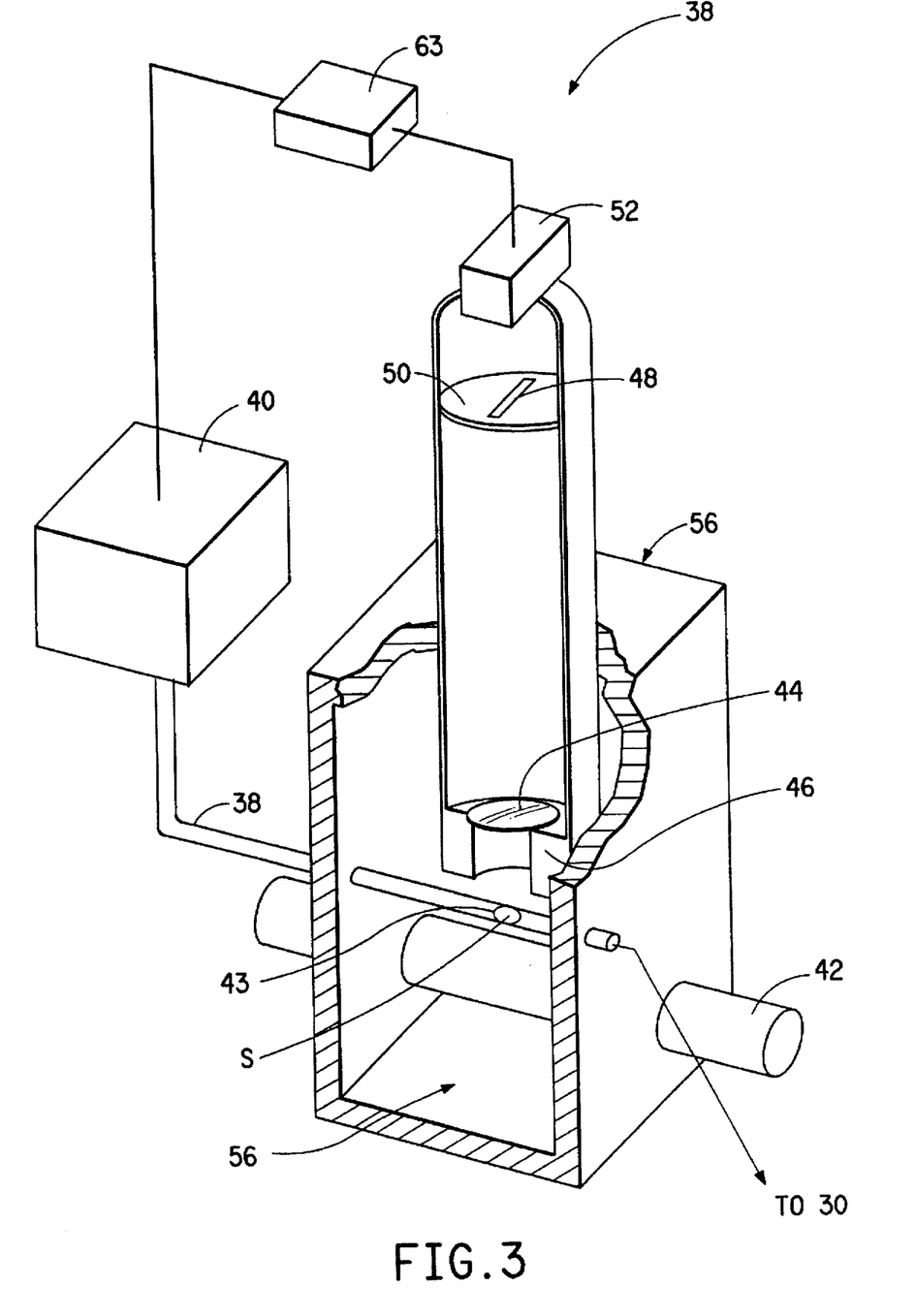
FIG. 3 is a perspective schematic view, partially in cross-section, of a liquid handling apparatus of the present invention.

FIG. 3 illustrates a liquid measuring apparatus 37 of the present invention for measuring and/or controlling the volume of either or both a sample liquid or a reagent liquid, that is, measuring the volume of a sample liquid or of a reagent liquid and controlling the volume of a sample liquid or of a reagent liquid, as they are provided to the reaction cuvette 18 using the sample liquid probe 30 and/or the reagent liquid arm 36.

A portion of tubing 38, typically capillary sized for small volumes, having first and second open ends and is conventionally arranged to have its first open end in liquid communication with a pumping means 40 and its second open end in liquid communication with the liquid probe 30 (FIG. 2), as indicated by the arrow of FIG. 3. Tubing 38 is necessarily at least transparent to radiation and is preferably formed of glass capillary material, available from Bel-Art Products, Pequannock, New Jersey. For the instance that tubing 38 is employed to pump body fluids, such as serum, a tubing made of glass and having dimensions 0.060 inch outer diameter and 0.020 inch inner diameter has been found to be useful. The tubing 38 passes through a measuring housing 56.

A radiation source 42 is positioned within the housing 56 parallel to and nearby the transparent tubing 38. Preferably radiation source 42 is a linear filament with an energy density in the range 1.9 to 12.5 lumens. An example of a commercial radiation source suitable for performing the present invention is the Gilway axial lead lamp, model 7159, available from Gilway Technical Lamps, Woburn, Mass. The radiation source 42 is located relative to the transparent tubing such that the radiation wave (a plane electromagnetic wave) incident upon transparent tube 38 is refracted from the inner wall of tube 38 in the direction of a photodetector 52. Thus, the location of the light source 42 is best defined in terms of the direction of the refracted wave (which is determined by the location of the photodetector 52), when the tube 38 contains no liquid (it is normally filled with air or like gas having a similar refractive index to maximize the refraction of the incident wave). The light source 42 is located at an azimuthal angle Ø (FIG. 4a), which is the angle between the incident wave from the light source 42 and the refracted wave from the inner wall 39 of the tube 38, that maximizes the light reaching the photodetector 52. An optical lens 44 is disposed vertically in a housing 46 (FIG. 3) relative to the transparent tubing 38 in optical alignment with radiation beam 49 as refracted from the transparent tubing 38 to provide for magnifying the radiation image refracted from the tube by a factor ranging between 1 and 100 times. Optical lens 44 is preferably a double convex lens having a focal length of 3.0 mm adapted to cause a 10-times magnified image of the refracted radiation lying on an optical axis 45 that passes to the defecting means 52 to be incident upon aperture 48. Exemplary of such lens is a double convex lens available as model A32023 from Edmund Scientific, Atlanta, Ga.

A collimating opening 48 having dimensions about 250 microns by 3 mm in a disk 50 of opaque material such as stainless steel of thickness 0.013 inches, the opening 48 being centrally aligned in housing 46 along the optical axis 45 with the center of the refracted radiation beam 49. Detecting means 52 is positioned at the top of housing 46 to intercept the refracted radiation beam 49. Detecting means 52 is preferably a photodetector 52 based on phototransistor conversion from radiation energy into electrical energy, Motorola part #MRD360 having been found to perform satisfactorily in the present invention. Motorola part #MRD360 has a minimum radiation sensitivity of about 12 ma at 0.5 mW/cm$^2$ over a range of radiation wavelengths from about 0.5 micron to about 1.0 microns, is of NPN construction and provides a Darlington output with a 40 usec response time. This particular device is preferred because of its suitability for direct coupling to logic electronics. The preferred phototransistor also includes in its construction an integrated lens to improve the efficiency of its angular radiation collection.

The interior surface of housing 46 may be coated with black tinted aluminum oxide to minimize any extraordinary radiation. Again, for assembly purposes, the hollow housing 46 may be secured as shown within a mounting block 56 in a fixed relationship with the transparent tubing 38 and radiation source 42.

The measuring apparatus (FIG. 3) is seen to include means for exposing the tube to radiation incident onto the tube and means to detect the amount of radiation refracted from the inner surface 39 (best seen in FIGS. 4a and 4b) of the tube 38. The invention relies on the fact that the incident wave 49 (FIG. 4b) is refracted less when the tube 38 is filled with a liquid rather than with gas(air). The decreased refraction prevents the refracted wave from being detected by photodetector 52. In practicing the present invention, a liquid sample segment S, having a leading edge 41 and a trailing edge 43, is pumped using pumping means 40 through the tube 38 to the sample liquid probe 30. The amount of radiation refracted from the inner surface 39 of the tube 38 through a magnifying lens 44 and the center opening 48 of a collimating aperture 50 before being detected using a single radiation detector 52.

Figure 4A:
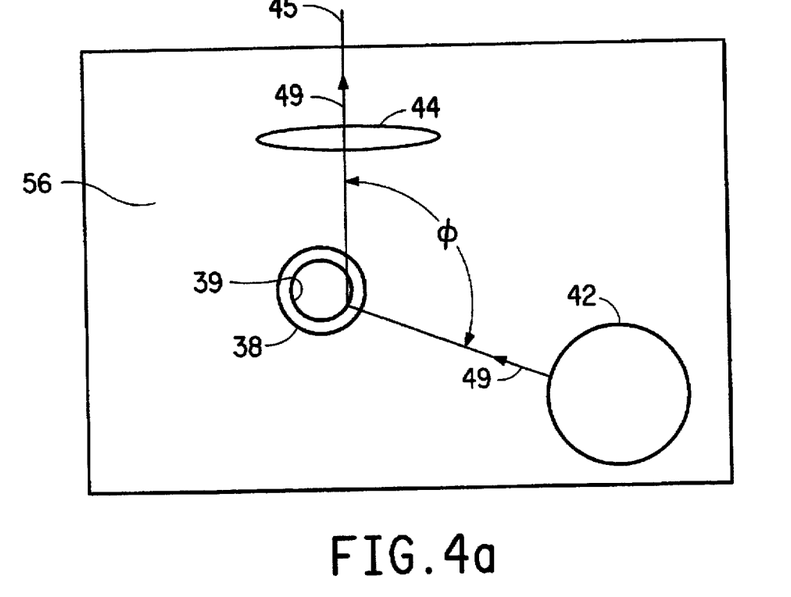
FIGS. 4a and 4b. are schematic cross-sectional views of the liquid handling apparatus of FIG. 3.
Figure 4B:
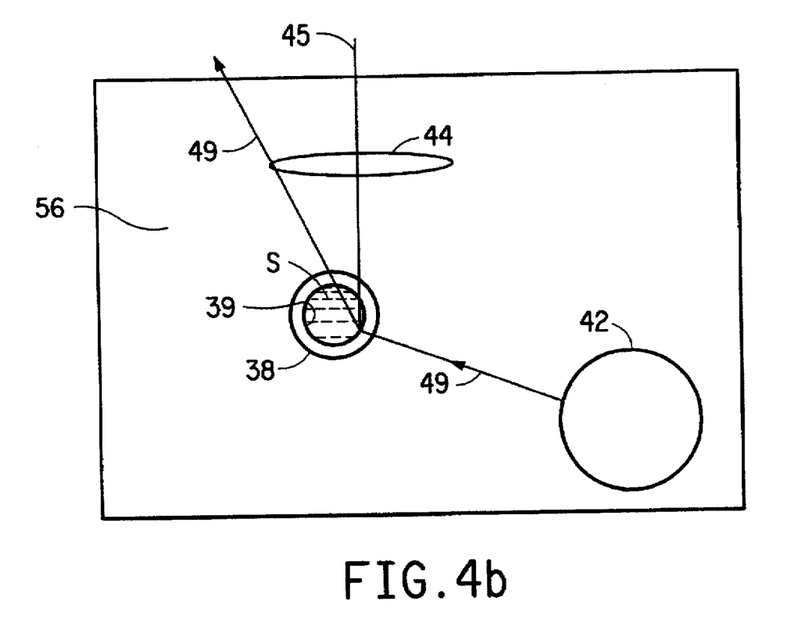
Figure 5:
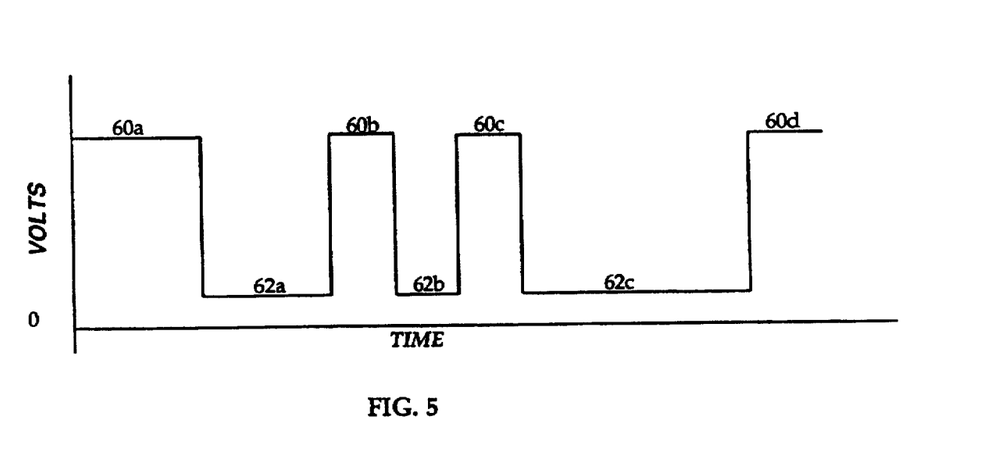
FIG. 5 is a graph depicting the signals generated within the liquid handling apparatus of FIG. 3; and, FIG. 6 is a graph depicting the relationship between signals generated within the liquid handling apparatus of FIG. 3 and the volume of liquid segments therein.

The operation of the liquid measuring apparatus 37 shown in the figures may be understood by reference to FIG. 4a, FIG. 4b, and FIG. 5. As used herein, the term "pumping" or the term "traversing" should be considered as including forcing a volume of a liquid to move through a length of tubing, as moving a precisely controlled volume of sample liquids from a sample liquid container, as aspirating a precisely controlled volume of sample liquid into a sample liquid container, as extracting a precisely controlled volume of reagent liquids from a reagent liquid container, and as aspirating a precisely controlled volume of reagent liquid into a reagent liquid container. It should be appreciated that the sample liquid container and/or reagent liquid container may comprise a single reaction vessel. Additionally, the term "pumping" should be considered as including manipulating the operation of a pumping device so as to cause a precisely controlled volume of sample liquid or reagent liquid to traverse a hollow tube.

FIG. 4a illustrates a key feature of the present invention wherein the inner surface 39 of the transparent tubing 38, the central optical axis of magnifying lens 44, the opening 48 of collimating aperture 50, and the detecting means 52, preferably a photodetector 52, are positioned to form a straight line 45 which lies within the refracted wave from an open or empty tube 38. The position of the radiation source 42, as defined hereinabove; i.e., a maximum portion of planar radiation wave 49 emanating from radiation source 42 is refracted at the interface between the inner surface 39 of the transparent tubing 38 and the interior of the transparent tubing 38 when the transparent tubing 38 contains no liquid. Consequently, planar radiation wave 49 refracted from the inner surface 39, toward and through lens 44, along line 45, then through collimating opening 48, and then onto detector 52 will generate a maximum signal voltage 60n; i.e. 60a, 60b, 60c, . . . 60n, as illustrated in FIG. 5. The present invention may be implemented with tubing 38 being composed of many materials and have a range of dimensions, as it is only critical that the tubing 38 be suitable for refracting radiation at a first angle when the tubing is not carrying a liquid and for refracting radiation at a different angle when the tubing is carrying a liquid.

FIG. 4b illustrates the converse of this key feature of the present invention as existing whenever the transparent tubing 38 contains a liquid segment S. In this instance, the index of refraction of the liquid is different from that of an open tube and the major portion of radiation wave 49 emanating from radiation source 42 is refracted at the interface between the inner surface 39 of the transparent tubing 38 and the liquid being pumped therein in a direction away from the magnifying lens 44, the collimating opening 48, and the detector 52. It has been discovered that the indices of refraction of nearly all liquid segments S amenable to being pumped are generally sufficiently different from the index of refraction of air so that the major portion of radiation is refracted from the inner surface interface in a direction away from the center of optical lens 44. Since the incident wave 49 is refracted away from lens 44, photodetector 52 generates a minimum signal voltage 62n; i.e. 62a, 62b, 62c, . . . 62n, as illustrated in FIG. 5, the minimum signal voltage 62n being significantly smaller than the previously measured maximum signal voltage 60n. Thus, the appearance of the leading edge 41 and trailing edge 43 of a liquid segment S of interest may be determined more precisely than in the prior art with the further advantage that only a single detector is required.

Accordingly, as illustrated in FIG. 5, the single photodetector 52 may be used to precisely determine the leading edge 41 and trailing edge 43 of a liquid segment by measuring the amount of incident wave 49 refracted from the inner surface 39 of the tube into alignment with photodetector 52. A voltage signal will be generated by photodetector 52 as indicated by section 60n. Pump 40 is activated to cause a segment S of liquid to traverse or move through the tubing 38 at a constant velocity. The pumping means 40 applies a volumetric displacement to the fluid in the tube. This displacement is conventionally measured in the art by measuring the distance traveled by an actuator not shown but employed within the pump. The actuator can be any conventional motion control device whose motion can be measured using a variety of means well known in the art. For example, in the preferred case of the actuator being selected as a conventional stepper motor, the sum of step pulses the movement of the stepper motor actuator is proportional to the distance traveled. The number of step pulses may be supplied and counted using a conventional pulse controller as is well known in the art. See for example, "Step Motor and Servo Motor Systems and Controls", pages A28–30, Parker Motion Control, 1995. In practicing the present invention, the pulse controller operates so that displacement of the actuator within pumping means 40 imparts a constant velocity to the slug as it travels through the tube 42.

The counted step pulse that is created as the image of the leading edge 41 of the segment S enters the optical magnifier is used as a signal to begin counting displacement of the pumping means 40. Each displacement of an actuator within the pumping means 40 corresponds to a constant volume of fluid displaced. Counting continues until the image of the trailing edge 43 of the segment S enters the optical magnifier is encountered. The total number of increments counted between the image of the leading edge 41 and the image of the trailing edge 43 is linearly proportional to the volume that traversed the optical field of view.

As would be expected, the volumetric resolution of the system is dependent on the optical resolution of the magnifier system and to the resolution of the actuator. The resolution of the system has been discovered to also be related to the internal diameter of the tube 38, as a reduced diameter is associated with a smaller cross-sectional volume and therefore a higher linear travel of the segment, per unit volume of fluid. All of these parameters may be optimized around the particular measurement resolution required; however no particular design is required, the present invention depending solely on using a single detecting means to detect the radiation refracted at a single position on the inner surface 39 of the tube 38, the radiation being refracted in a direction different from a direction corresponding to a maximum value of refracted radiation, essentially independent of the optical characteristics of the fluid being pumped.

As mentioned hereinbefore, the angle Ø between the incident wave 49 and the rectracted wave 49 and the straight line 45 is selected so that a maximum amount of the incident wave 49 is refracted from the inner surface 39 of the tubing 38 toward the photodetector 52 when there is no liquid with the tubing 38. It has been discovered that the accuracy of the liquid segment S volume may be determined to within +/−10 nanoliters when an optical resolution of the magnifier system, the resolution of the actuator, and the internal diameter of the tube 38 have values described hereinbelow. Further, because the present invention depends on the radiation refracted from the inner surface 39 of the tube 38 being at a maximum value when there is no liquid in the tube 38, a great variety of liquids may be supplied through tube 38 without placing restrictions on the radiation absorption characteristics of the liquids being pumped. This is an important feature not found in liquid volume measuring systems of the prior art which are seen to place restrictions on the optical or absorption characteristics of the liquids meing measured and/or peumed. In addition, different calibration procedures are not required when different liquids are being pumped. Hence, the present invention has made it possible to routinely measure or control the traversing of the liquid so that the volumes of a plurality of consecutive liquid segments have a constant volume to within +/−10 nanoliters for a broad range of liquids comprising segment S, including whole blood, serum, urine, water, glycerol, and aqueous reagents.

The low voltage signal, generated in the presence of fluid in the detector, enables a counting means such as a conventional pulse counter 63 to begin counting actuator increments. When the trailing edge of the segment S reaches the section of the tubing 38 being exposed to radiation, the radiation refracted from the inner surface 39 of the tube will again be refracted into alignment with photodetector 52 and a maximum voltage 60n is generated by photodetector 52. The high voltage signal disables the pulse counter 63. The total number of pulses counted is proportional to the amount of fluid transferred through the detector.

Figure 6:
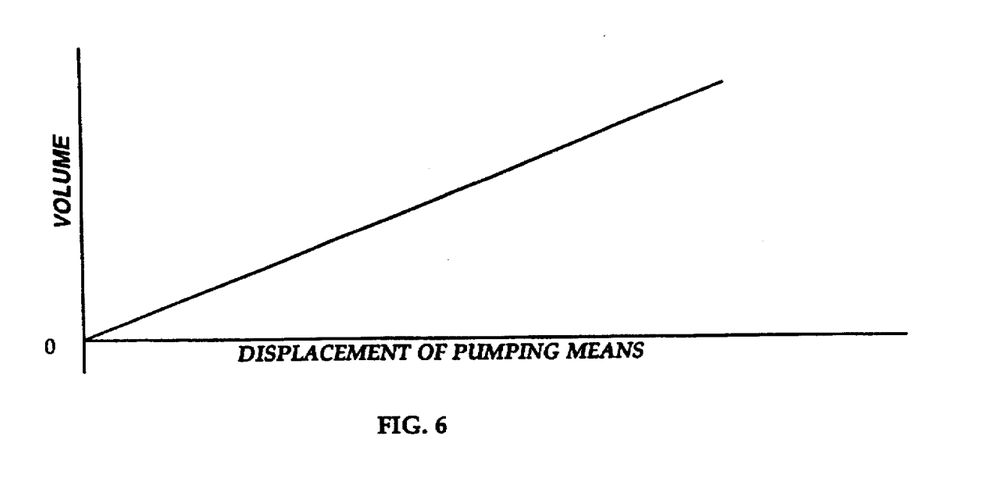

It will be readily appreciated by those skilled in the art that calibration between the number of pulses counted by the pulse counter 63 while the liquid segment S is traversing the section of the tubing 38 being exposed to radiation, as gated by the minimum volume of the signal 62n, and the volume of the segment S is a straightforward process. FIG. 6 shows such a straight-line relationship, determined in the instance of a stepper motor controlled pump, such as the Dimension® Dual Pump module supplied by E. I. DuPont de Nemours, Wilmington, Del. In addition, logic means 64, best seen in FIG. 3, connected between the output of photodetector 52 and the pumping means 40, may be adapted to control the operation of the pumping means 40 to provide for controlling the traversing of the liquid so that the volumes of a plurality of consecutive liquid segments are a constant volume. Furthermore, a desired volume of a liquid segment S may be obtained by maintaining pumping means 40 in a pumping mode for a correlated number of pulses of measuring minimum voltage signal 62n. FIG. 5 illustrates, for example, three different minimum voltage signals 62a, 62b, 62c, corresponding to three different liquid segment S volumes, the third, corresponding to 62c, being the largest and the second, corresponding to 62b, being the smallest.

In the particular application of pumping within an automated clinical analyzer, using glass tubing with an internal volume of 5 uL, radiation as identified above, and an angle Ø of about 115 degrees, the present invention has been useful in delivering a series of liquid segments with constant volumes between about 0.3 and 1.2 uL at an accuracy of ±10 nL. Opening 48 is sized as described above to obscure an amount ranging between 60 and 99 percent of the radiation that is off the central axis of the image of the conduit and to pass the radiation that is parallel to the optic axis. This provision for collimating the radiation beam 49 refracted from the tube by an amount ranging between 60 and 99 percent, preferably between 90.0 and 99.9 percent, is an important feature in achieving the high resolution detection of the fluid edge and in precisely controlling the displacement of the pumping means 40 delivering liquid segment S. In this case, a stepper motor controlled syringe pump 40 having a total volume of 100 uL was controlled by a microstepping system having a resolution of 10,000 cts/ revolution. The overall resolution of the step counting system is 8 counts/nL.

Additionally, flexible tubing made from an elastomer under the tradename C-FLEX by Concept Polymer Technologies of Clearwater, Fla. having an internal diameter of 0.030 inches and an outside diameter of 0.065 inches has been tested. Using such tubing and having radiation incident at an angle of 25 degrees, similar edge resolution has been obtained using the actuating device described previously. The advantage of the flexible conduit relates to its simplicity of interface with other parts of the diagnostic analyzer 10.

For assembly purposes, the lens 44, disk 50 and photodetector 52 are mounted inside a closed, hollow column 54, the interior surface of which may be coated with black tinted aluminum oxide to minimize any extraordinary radiation. Again, for assembly purposes, the hollow column 54 may be secured as shown within a mounting block 56 in a fixed relationship with the transparent tubing 38 and radiation source 42.

The independence of the present invention from the radiation refraction characteristics of the liquid being pumped through tubing 38 advantageous allows for many liquids to be supplied through 38 without requiring re-calibration procedures. Importantly also, the present invention provides for accurately determining the volume of a liquid segment in a tube using a simplified arrangement having only a single radiation detection station. Those skilled in the art, having the benefit of the teachings of the present invention as hereinabove set forth may effect numerous modifications thereto. It should be understood that these and other modifications lie within the scope of the present invention as set forth in the appended claims.

What is claimed is:

1. A method for determining the volume of a liquid segment traversing at a constant velocity through a transparent tube having an inner wall using a radiation detector, the segment having a leading edge and a trailing edge, comprising the steps of:

exposing the tube to an incident wave from a source of radiation;

locating the source of radiation at an azimuthal angle Ø that maximizes the amount of radiation reaching the detector, the angle Ø being the angle formed between the incident wave from the source of radiation and the refracted wave from the inner wall of the tube;

detecting refracted waves from the source that are refracted at the inner wall of the tube; and, comparing the amount of radiation refracted from the tube at the leading and trailing edges of the segment with the amount of radiation refracted from the tube when there is no liquid segment within the tube, so that the volume of the segment may be determined from the time interval between passage of the leading and trailing edges of the segment past a position along the tube, in combination with the internal diameter of the tube and the constant velocity of the segment.

2. The method of claim 1 further comprising the step of magnifying the beam refracted radiation from the tube by a factor ranging between 1 and 100 times before the step of detecting measuring the amount of radiation.

3. The method of claim 1 further comprising the step of collimating the beam refracted radiation from the tube by an amount ranging between 60 and 99 percent before the step of detecting the amount of radiation.

4. The method of claim 1 further comprising controlling the traversing of the liquid so that the volumes of a plurality of consecutive liquid segments are a constant volume.

5. The method of claim 1 wherein the volume of the liquid segment is in the range of 100 nanoliter to 1 microliter.

6. The method of claim 1 wherein the radiation has wavelengths between 0.4 and 1.2 microns.

7. The method of claim 1 wherein the liquid segment comprises liquids having a refractive index in the range 1 to 1.8.

8. The method of claim 1 wherein the liquid segment comprises whole blood, serum, urine, water, glycerol, or aqueous reagents.

9. An apparatus for determining the volume of a liquid segment traversing at a constant velocity through a transparent tube having an inner wall, the segment having a leading edge and a trailing edge, comprising:

- a single radiation detector for measuring an amount of radiation refracted from the inner wall of the tube;
- a source of radiation located at an azimuthal angle Ø that maximizes the amount of radiation reaching the detector, the angle Ø being the angle formed between the source of radiation and the radiation refracted from the inner wall of the tube; and,
- means for comparing the amount of radiation refracted from the inner wall of the tube at the leading and trailing edges of the segment with the amount of radiation refracted from the inner wall of the tube when there is no liquid segment within the tube, so that the distance between the leading and trailing edges of the segment traversing past a position along the tube may be determined from the constant velocity.

10. The apparatus of claim 9 further comprising means for controlling the traversing of the liquid so that the volume of the liquid segment is a predetermined volume.

11. The apparatus of claim 9, further comprising means for magnifying the radiation refracted from the tube by a factor ranging between 1 and 100 times.

12. The apparatus of claim 9, further comprising means for collimating the radiation refracted from the tube by an amount ranging between 60 and 99 percent.

13. The apparatus of claim 9 wherein the radiation has wavelengths between 0.4 and 1.2 microns.

* * * * *

UNITED STATES PATENT AND TRADEMARK OFFICE
CERTIFICATE OF CORRECTION

PATENT NO. : 5,724,142
DATED : March 3, 1998
INVENTOR(S) : Edward Stephen Kaminski, et. al.

It is certified that error appears in the above-identified patent and that said Letters Patent is hereby corrected as shown below:

Column 1, Line 19: Delete "bet-ween" and insert --between--.

Column 7, Line 16: Delete "60nis" and insert the phrase --60n is--.

Column 8, Line 53: Delete "measuring".

Signed and Sealed this

Tenth Day of November 1998

Attest:

BRUCE LEHMAN

Attesting Officer　　　　Commissioner of Patents and Trademarks